US012642698B2

(12) United States Patent
Rathjen et al.

(10) Patent No.: US 12,642,698 B2
(45) Date of Patent: Jun. 2, 2026

(54) OPHTHALMOLOGICAL LASER DEVICE

(71) Applicant: Ziemer Ophthalmic Systems AG, Port (CH)

(72) Inventors: Christian Rathjen, Bremen (DE); Michael Steinlechner, Zurich (CH)

(73) Assignee: Ziemer Ophthalmic Systems AG, Port (CH)

( * ) Notice: Subject to any disclaimer, the term of this patent is extended or adjusted under 35 U.S.C. 154(b) by 318 days.

(21) Appl. No.: 18/238,563

(22) Filed: Aug. 28, 2023

(65) Prior Publication Data

US 2024/0130893 A1    Apr. 25, 2024
US 2024/0225896 A9    Jul. 11, 2024

(30) Foreign Application Priority Data

Oct. 20, 2022    (CH) ................................ 001244/2022

(51) Int. Cl.
*A61F 9/008*        (2006.01)
*A61B 18/20*        (2006.01)
*A61B 18/22*        (2006.01)
(52) U.S. Cl.
CPC ............ *A61F 9/008* (2013.01); *A61B 18/203* (2013.01); *A61B 18/22* (2013.01); *A61B 2018/2015* (2013.01); *A61B 2018/205547* (2017.05); *A61F 2009/00897* (2013.01)
(58) Field of Classification Search
CPC ........... A61F 9/008; A61F 2009/00897; A61B 18/203; A61B 18/22; A61B 2018/2015; A61B 2018/205547
See application file for complete search history.

(56) References Cited

U.S. PATENT DOCUMENTS 10,092,445 B2    10/2018    Rathjen et al.
2016/0317349 A1*  11/2016    Rathjen ................. A61B 90/50
2017/0340483 A1   11/2017    Rill et al.

FOREIGN PATENT DOCUMENTS

EP          1731120 A1    12/2006
EP          2111198 A1    10/2009
WO      2008098388 A1     8/2008

OTHER PUBLICATIONS

Jan. 19, 2023—(CH) Search Report—App 12442022.

* cited by examiner

*Primary Examiner* — John R Downey
*Assistant Examiner* — Sebastian X Lukjan
(74) *Attorney, Agent, or Firm* — Banner & Witcoff, Ltd.

(57)                ABSTRACT

An ophthalmological laser device for treatment of eye tissue is disclosed, comprising a base station having a treatment laser source configured to generate a treatment laser beam, an application head, an arm arranged between the base station and the application head, wherein the arm is configured to provide a beam path for the treatment laser beam, the arm having at least one joint, and a scanner arranged in the joint and configured to dynamically deflect the treatment laser beam about two axes, wherein the treatment laser beam upstream of the scanner is collinear with an axis of rotation of the joint and an orientation of the scanner is dependent on a movement of the joint.

15 Claims, 6 Drawing Sheets

OPHTHALMOLOGICAL LASER DEVICE

CROSS-REFERENCE TO RELATED APPLICATION

The present application claims priority to and the benefit of Switzerland Patent Application 001244/2022 filed Oct. 20, 2022, which is incorporated by reference in its entirety herein.

FIELD OF THE DISCLOSURE

The present disclosure relates to an ophthalmological laser device.

BACKGROUND OF THE DISCLOSURE

Ophthalmological treatment devices, which use a laser for eye treatment, are known. The ophthalmological treatment device has a laser source, which produces a pulsed laser beam. Additionally, the wavelength of the laser light produced by the ophthalmological treatment device is dependent on the type of eye treatment and is typically in the ultraviolet (190 nm to 230 nm) or infrared (780 nm to 1100 nm) range.

The laser beam is typically produced by a laser source arranged in a base station. The laser beam is dynamically deflected by a scanner arranged in the base station, downstream from the laser source, to generate the desired treatment pattern. The laser beam is then guided along a beam path in an arm to an application head, where the laser beam is focused onto a patient's eye. To flexibly position the application head over a reclined patient, the arm is typically maneuverable, having one or more joints or articulations. At each joint, a mirror serves to deflect the laser beam along the beam path such that it reaches the application head.

Each component of the ophthalmological treatment device which interacts with the laser beam between the laser source and the patient's eye decreases the power of the laser, as each component absorbs or deflects at least part of the laser beam. Additionally, each component which interacts with the laser beam must be precisely designed, positioned, and often maintained to ensure reliable and safe operation of the ophthalmological treatment device which, being a device used for surgery, places high demands on the components. Due to the large number of components required and the required precision, ophthalmological laser devices are complex.

Therefore, there is a constant need and desire to reduce the complexity of an ophthalmological laser device, in particular by reducing the number of required components along the beam path.

SUMMARY OF THE DISCLOSURE

The disclosure and embodiments disclosed herein to provide an ophthalmological laser device having a scanner.

In particular, the disclosure and embodiments disclosed herein provide an ophthalmological laser device which does not have at least some of the disadvantages of the prior art, in particular in that it has fewer components.

The present disclosure relates to an ophthalmological laser device for treatment of eye tissue. The ophthalmological laser device comprises a base station having a treatment laser source configured to generate a treatment laser beam. The ophthalmological laser device comprises an application head. The ophthalmological laser device comprises an arm arranged between the base station and the application head. The arm is configured to provide a beam path for the treatment laser beam, the arm having at least one joint. The ophthalmological laser device comprises a scanner arranged in the joint and configured to dynamically deflect the treatment laser beam about two axes, wherein the beam path of the treatment laser beam upstream of the scanner is collinear with an axis of rotation of the joint and an orientation of the scanner is dependent on a movement of the joint.

In an embodiment, the scanner comprises a deflecting element pivotable about the two axes.

In an embodiment, the scanner comprises a first deflecting element pivotable about the first axis and a second deflecting element pivotable about the second axis.

In an embodiment, the joint comprises an upstream, with respect to the base station stationary joint part and a downstream movable joint part. The scanner is arranged at the joint by being coupled to the downstream movable joint part such that the scanner moves together with the downstream movable joint part.

In an embodiment, the scanner is coupled to the joint by way of a coupling, in particular a mechanical coupling.

In an embodiment, the treatment laser beam incident on the scanner is a collimated treatment laser beam.

In an embodiment, the treatment laser beam deflected by the scanner is a collimated treatment laser beam. The collimation is achieved, for example, by way of a laser collimator arranged in the beam path. The laser collimator is preferably arranged in the base station.

In an embodiment, the arm includes an upstream arm segment which is upstream from the joint and a downstream arm segment which is downstream from the joint. The treatment laser beam in the upstream arm segment is collinear with a centerline of the upstream arm segment. The scanner is arranged such that treatment laser beam in the downstream arm segment is collinear with a centerline of the downstream arm segment, regardless of a movement of the joint, when the scanner is in a zero-position. The zero-position is a default position in that the scanner does not steer the treatment laser beam off a center axis of the beam path.

In an embodiment, the ophthalmological laser device further comprises a mirror arranged in the upstream stationary joint part, the mirror being configured to deflect the treatment laser beam onto the scanner.

In an embodiment, the joint has an axis of rotation which is not collinear with a centerline of the upstream arm segment and the mirror is configured to deflect the treatment laser beam in a direction collinear with the axis of rotation of the joint and coincident with the scanner.

In an embodiment, the joint is rotatable about a first axis and a second axis. The mirror is coupled to the joint such that the mirror rotates about the first axis. The scanner is coupled to the joint such that the scanner rotates about the second axis.

In an embodiment, the arm comprises a plurality of joints arranged between the base station and the application head, and the scanner is arranged in the particular joint adjacent to the application head.

In an embodiment, the scanner comprises an electromagnetic scanner, in particular a galvano scanner, more particularly a dual-axis galvano scanner.

In an embodiment, the scanner comprises a piezoelectric scanner.

In an embodiment, the scanner comprises an electrostatic scanner.

BRIEF DESCRIPTION OF THE DRAWINGS

The herein described disclosure will be more fully understood from the detailed description given herein below and the accompanying drawings, which should not be considered limiting to the disclosure described in the appended claims. The drawings in which:

DESCRIPTION OF THE EMBODIMENTS

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figure 1:
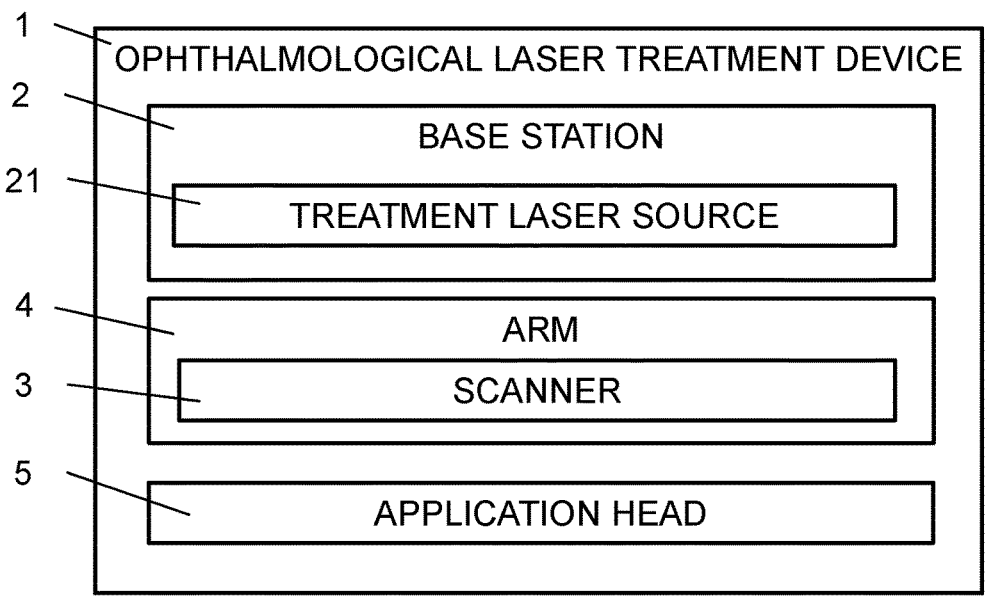
FIG. 1 shows a block diagram illustrating schematically an ophthalmological laser device having a scanner.
Figure 2:
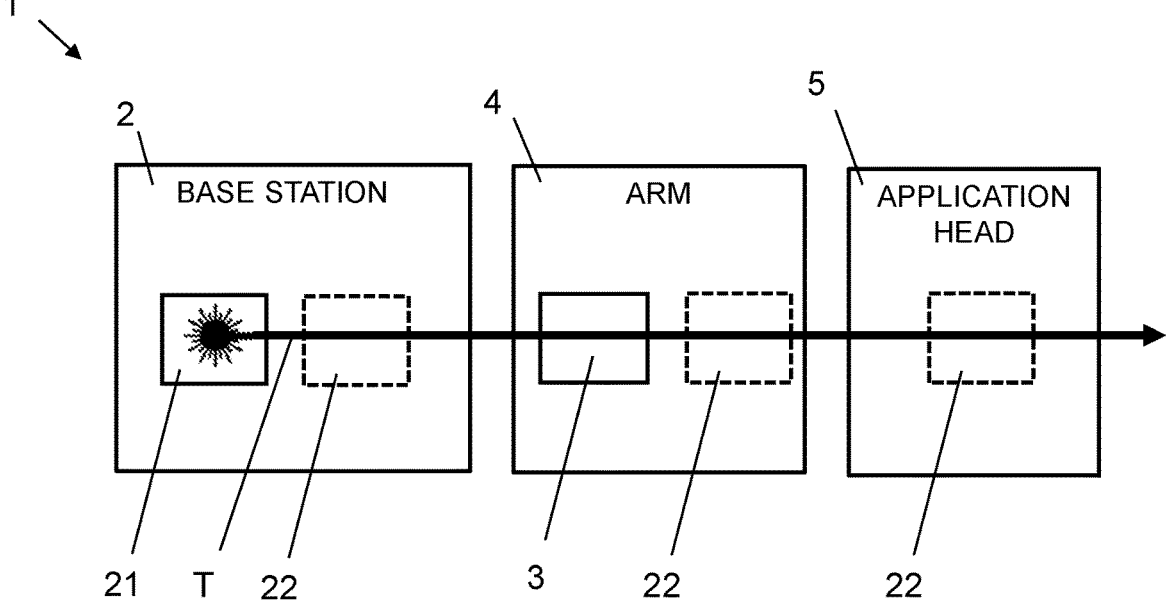
FIG. 2 shows a block diagram illustrating schematically a beam path of the treatment laser through the ophthalmological laser device with the scanner arranged in the arm.

FIGS. 1 and 2 show block diagrams illustrating schematically an ophthalmological laser device 1. FIGS. 1 to 9 schematically illustrate modules and/or elements of various embodiments of the ophthalmological laser device 1 and provide exemplary sequences or arrangement of modules and/or elements, including modules and/or elements in a beam path. The skilled person understands that at least some modules and/or elements shown in a particular figure may be combined with modules and/or elements shown in another figure.

The ophthalmological laser device 1 comprises a base station 2. The base station 2 is configured as a fixed or mobile apparatus. The ophthalmological laser device 1 has a treatment laser source 21 arranged in the base station 2 which generates a treatment laser beam T. The base station further includes, for example, a power supply and other auxiliary subsystems necessary for operation of the ophthalmological laser device 1.

The treatment laser source 21 is configured to, for example, generate an ultraviolet treatment laser beam T having a wavelength of between 190 nm and 230 nm. For example, the treatment laser source 21 comprises an excimer or a solid-state laser which produces such an ultraviolet treatment laser beam T. The excimer laser uses a combination of a noble gas and a reactive gas under high pressure and electrical stimulation to generate the treatment laser beam T. In particular, an excimer laser using argon as the noble gas and fluoride as the reaction gas may be used as the treatment laser source 21.

In another example, the treatment laser source 21 is configured to generate an infrared treatment laser beam T having a wavelength of between 780 nm and 1100 nm. For example, the treatment laser source 21 comprises a solid-state laser, such as a Ti:Sa or Ytterbium laser. The treatment laser source 21 will not be described in further detail, however the skilled person is aware that the treatment laser source 21 can comprise, for example, a gain medium, a laser resonator, a laser pump, a pulse generating element, cavity mirrors, coupling mirrors, wavelength tuners, and/or a frequency converter (including one or more non-linear optical crystals) or fiber optical elements.

In an embodiment, the treatment laser beam T is a pulsed laser beam.

In an embodiment, the treatment laser beam T is a collimated treatment laser beam.

In an embodiment, the treatment laser source 21 is configured to generate femtosecond laser pulses, which have pulse widths of typically from 10 fs to 1000 fs (1 fs=$10^{-15}$ s).

The ophthalmological laser device 1 comprises an application head 5. The application head 5 is designed to guide the treatment laser beam T into or onto the eye 91 of a patient 9 (as shown, for example, in FIGS. 3 to 5). The application head 5, for this purpose, can comprise focusing optics configured to focus the treatment laser beam T onto one or more treatment points inside or on the eye tissue, in particular the cornea for a pointwise tissue disruption or ablation. The focusing optics comprise a lens system having one or more optical lenses or mirrors. Depending on the embodiment, the focusing optics comprise one or more movable or deformable lenses and/or a drive for moving the entire focusing optics in order to set and adjust the focal depth, or the treatment height, in the projection direction along the projection axis.

In an embodiment, the application head 5 comprises a patient interface. The application head 5 is preferably fixed onto the eye 91 by means of the patient interface, for example using suction.

Alternatively, the application head 5 does not have a patient interface for direct contact with the eye 91, but the application head 5 and the eye 91 of the patient 9 are separated by an air gap of several centimeters, for example.

Depending on the embodiment, the ophthalmological laser device 1 (in particular, the application head 5) further comprises an eye tracker configured to track a position and/or orientation of the eye 91 of the patient 9.

Figure 3:
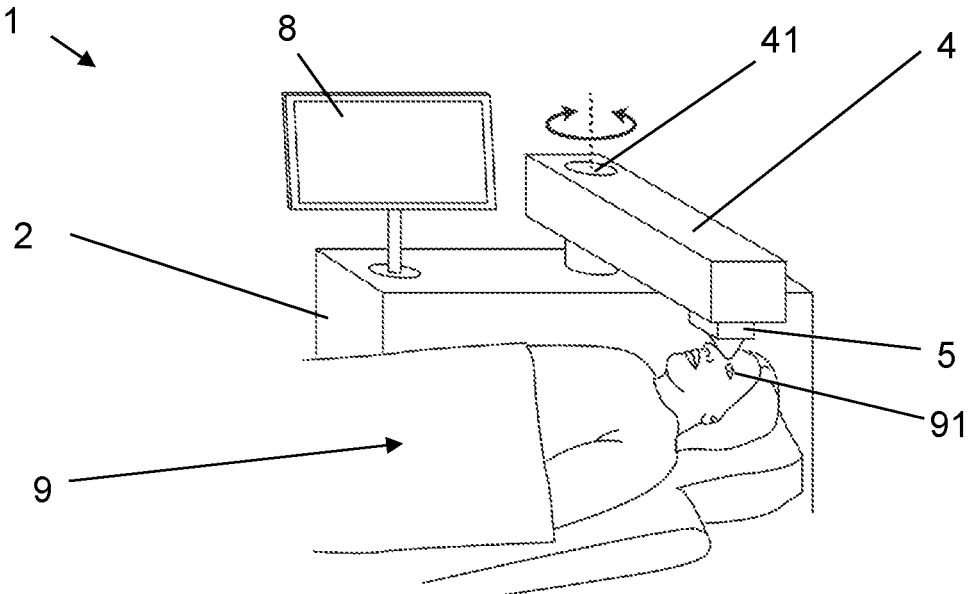
FIG. 3 shows a perspective view illustrating schematically an ophthalmological laser device having a horizontally rotatable arm with a single joint.
Figure 4:
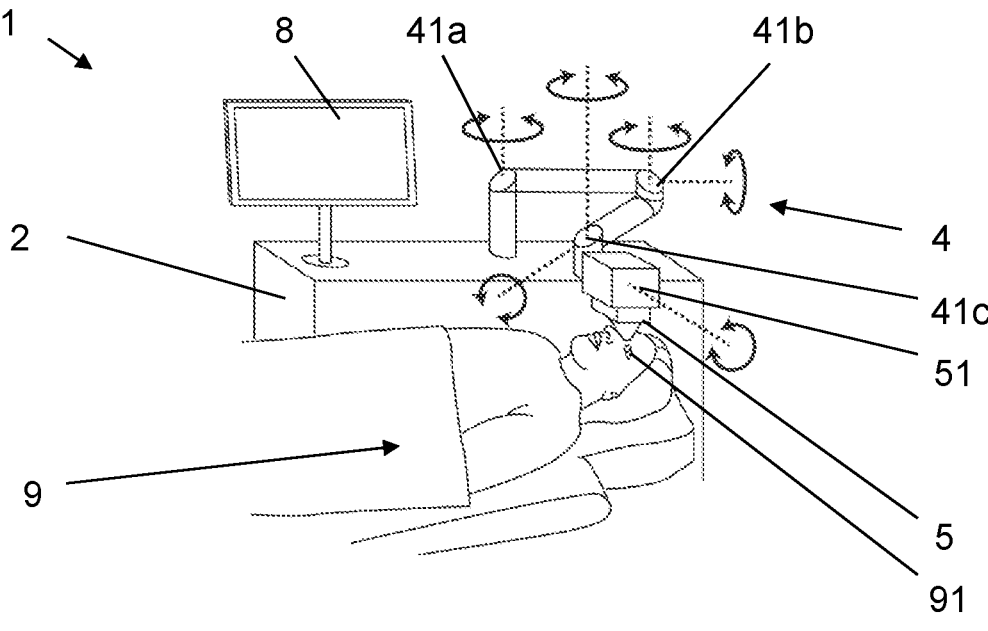
FIG. 4 shows a perspective view illustrating schematically an ophthalmological laser device having an articulated arm having multiple joints.
Figure 5:
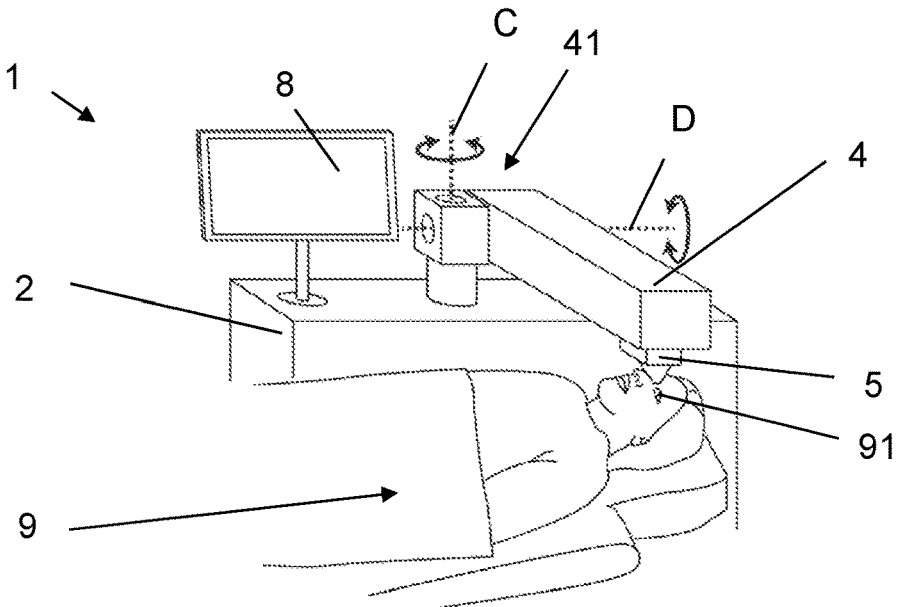
FIG. 5 shows a perspective view illustrating schematically an ophthalmological laser device having a vertically and horizontally rotatable arm with two joints.

The ophthalmological laser device 1 comprises an arm 4 arranged between the base station 2 and the application head 5. The arm 4 is configured to provide a beam path for the treatment laser beam T, such that the treatment laser beam T travels along the inside of the arm 4 from the base station 2 to the application head 5. The arm 4 comprises one or more joints 41 (as shown in FIGS. 3 to 5) such that the application head 5 is movable and/or rotatable with respect to the base station 2. The rotatable joints 41 may comprise mirrors 42 arranged in the beam path to reflect the treatment laser beam T along the arm 4.

The arm 4 includes a scanner 3 which is configured to steer the treatment laser beam T delivered by the treatment laser source 21 onto treatment points on a treatment pattern (comprising a laser trajectory). The arrangement of the scanner 3 in the arm is described in more detail with reference to FIGS. 6 to 8. The scanner 3 itself is described in more detail with reference to FIGS. 9 to 11.

In an embodiment, the ophthalmological laser device 1 comprises transmission optics arranged in the arm 4 and/or in the application head 5. The transmission optics are designed to work in conjunction with the scanner 3 to adapt the angular excursion of the ophthalmological laser device 1 to a treatment area and optionally to adjust the beam size.

The transmission optics in particular can be an afocal system or a system with conjugated images planes. The transmission optics comprise one or more lenses and/or mirrors and may further include a drive for adjusting a focus and/or a reduction of image size.

Because the treatment laser beam T is reflected by each mirror 42, for example the mirrors 42 in the arms 4, the treatment pattern generated by the scanner 3 is reflected and/or rotated according to the angles between the beam path and the mirror 42.

The ophthalmological laser device 1 is controlled by the control module (not shown), as described below in more detail, by controlling the treatment laser source 21 and the scanner 3, as well as by controlling additional modules 22 of the ophthalmological laser device 1 arranged in the beam path of the treatment laser beam T, as described with reference to FIG. 2 in more detail.

The control module is configured to transmit, to the treatment laser source 21, the scanner 3, and optionally to additional modules 22, control signals. The control signals include a laser control signal configured to control the treatment laser source 21 and a scan signal configured to control the scanner 3. The control signals can further include a beam shaper control signal, for example. The control signals are generated according to a treatment model which is designed for treating the eye 91 of a patient 9 using the ophthalmological laser device 1. The control signals are further generated according to operating specifications, operating parameters, monitoring routines and/or safety routines of the ophthalmological laser device 1. Additionally, the control module can be configured to receive, from the treatment laser source 21 and the scanner 3 (optionally also from the additional modules 22), feedback signals. The feedback signals include, for example, a measurement signal from the treatment laser source 21 indicating a laser power, as well as scanner feedback signals from the scanner 3, indicating, for example, a position, orientation, and/or motion of the scanner 3 (including its components) as described below in more detail.

In an embodiment, the control module is configured to check proper functioning of the scanner 3. The control module checks proper functioning using the control signals (in particular the scan signal) and the feedback signal (in particular, the scanner feedback signal). Thereby, the following parameters of the scanner 3 may be assessed by the control module: a zero position of the scanner 3, a maximum deflection angle in one or more axes, a minimum angular deflection step size (i.e. minimal increment of deflection) in one or more axes), a flatness of the deflecting element 31, a distortion of the deflecting element 31, a dynamic response of the scanner 3, or other properties of the scanner 3.

The control module is configured to control the ophthalmological laser device 1. The control module is preferably arranged in the base station 2. The control module embodies a programmable device and comprises, for example, one or more processors, and one or more memory modules having stored thereon program code, data, as well as programmed software modules for controlling the processors, and/or other programmable circuits or logic units included in the control module 3, such as ASICs (Application-Specific Integrated Circuits), GPUs (graphics processing units), and/or TPUs (tensor processing units). The memory modules comprise volatile and/or non-volatile storage media, for example random access memory and/or flash memory, respectively. The control module 3 is connected to other components and modules of the ophthalmological laser device 1 as disclosed herein, in particular the treatment laser source 21 and the scanner 3. The connection is a wired and/or wireless connection configured to exchange control signals and/or feedback signals.

The control module, depending on the embodiment, further comprises a communication interface. The communication interface is configured for data communication with one or more external devices. Preferably, the communication interface comprises a network communications interface, for example an Ethernet interface, a WLAN interface, and/or a wireless radio network interface for wireless and/or wired data communication using one or more networks, comprising, for example, a local network such as a LAN (local area network), and/or the Internet.

The control module performs one or more steps and/or functions as described herein, for example according to the program code stored in the one or more memory modules. Additionally, or alternatively, the program code can be wholly or partially stored in one or more auxiliary processing devices, for example a computer. The skilled person is aware that at least some of the steps and/or functions described herein as being performed on the processor of the ophthalmological laser device 1 may be performed on one or more auxiliary processing devices connected to the ophthalmological laser device 1 using the communication interface. The auxiliary processing devices can be co-located with the ophthalmological laser device 1 or located remotely, for example on a remote server computer.

The skilled person is also aware that least some of the data associated with the program code (application data) or data associated with a particular patient (patient data) and described as being stored in the memory of the ophthalmological laser device 1 may be stored on one or more auxiliary storage devices connected to the ophthalmological laser device 1 using the communication interface.

The control module stores, in the one or more memory modules, a treatment model. The treatment model is designed for treating the eye 91 of a patient 9 using the ophthalmological laser device 1. In particular, the treatment model defines a number of treatment points or treatment curves onto which the treatment laser beam T is directed.

Additionally, or alternatively, the control module is configured to store one or more predetermined thresholds related to properties of the ophthalmological treatment device 1, in particular the scanner 3. The predetermined thresholds indicate, for example, normal or allowable limits and/or ranges of properties of the scanner 3. Depending on the embodiment, the control module is configured to perform one or more actions if the allowable limits and/or ranges are not met. For example, an alarm can be triggered and/or a treatment aborted.

The ophthalmological laser device 1 optionally includes a user interface comprising, for example, one or more user input devices, such as a keyboard, and one or more output devices, such as a display 8 (as shown in FIGS. 3 to 5). The user interface is configured to receive user inputs from an eye treatment professional, in particular based on, or in response to, information displayed to the eye treatment professional using the one or more output devices.

FIG. 2 shows schematically how the treatment laser beam T travels through various modules of the ophthalmological laser treatment system. After being generated in the treatment laser source 21, the treatment laser beam T optionally passes through one or more additional modules 22 before entering the arm 4, where it is dynamically deflected by the scanner 3 before passing through the application head 5.

Depending on the embodiment, one or more additional modules 22 are arranged in the beam path inside the base station 2. The one or more additional modules 22 are arranged downstream from the treatment laser source 21. The additional modules 22 may also be arranged in the arm 4 and/or in the application head 5.

The additional modules 22 include a laser attenuator, a beam shaper, a divergence modulator, a beam expander, a frequency modulator, a beam diagnostics module, and a shutter.

The laser attenuator is configured to attenuate the treatment laser beam T.

The beam shaper is configured to control the laser beam profile, in particular to redistribute the irradiance and/or phase of the treatment laser beam T to attain a desired laser beam profile that is maintained along the propagation distance, in particular the propagation distance from the beam shaper to the eye 91.

The divergence modulator is configured to modulate the focal depth and thereby the treatment height, in the projection direction along a projection axis.

The beam expander is configured to alter a diameter of the treatment laser beam T along the beam path.

The shutter is arranged in the beam path and configured to stop the treatment laser beam T if an appropriate shutter signal is received.

FIGS. 3 to 5 show three different embodiments of the ophthalmological laser device 1, each having a different embodiment of the arm 4. Other embodiments are possible, and depending on the configuration of the base station 2, in particular whether the base station 2 is itself height-adjustable or not, certain aspects of at least some of the three embodiments described below can be modified. Specifically, certain joints 41 for adjusting a vertical height of the application head 5 are superfluous, depending on the embodiment, and may be omitted.

In FIG. 3, the arm 4 is rotatable about the joint 41, such that the arm 4 can swing horizontally over a reclining patient 9 such that the application head 5 is moved into position above the eye 91 of the patient 9.

In FIG. 4, the arm 4 is an articulated arm 4 rotatable about the joints 41*a*, 41*b*, 41*c* such that the application head 5 can be flexibly moved into position above the eye 91 of the patient 9. Each joint 41*a*, 41*b*, 41*c* enables one or more rotations, for example the joint 41*b* allows both a rotation in the vertical as well as the horizontal plane. Additionally, it can be seen that the application head 5 has a joint 51 about which the application head 5 can be rotated.

In an embodiment, the scanner 3 is arranged in the joint 41*c* adjacent to the application head 5, i.e. the last joint 41*c* of the arm 4 before the treatment laser beam T enters the application head 5. The scanner 3 may also be arranged in the last joint of the arm 4 independent of any particular embodiment of the arm 4.

In FIG. 5, the arm 4 is rotatable at the joint 41 about a first joint axis C such that the arm 5 can swing horizontally over a reclining patient 9. Thereby, the application head 5 is moved into position above the eye 91 of the patient 9. Additionally, the arm 4 is configured to perform a vertical movement at the joint 41 about a second axis D.

Figure 6:
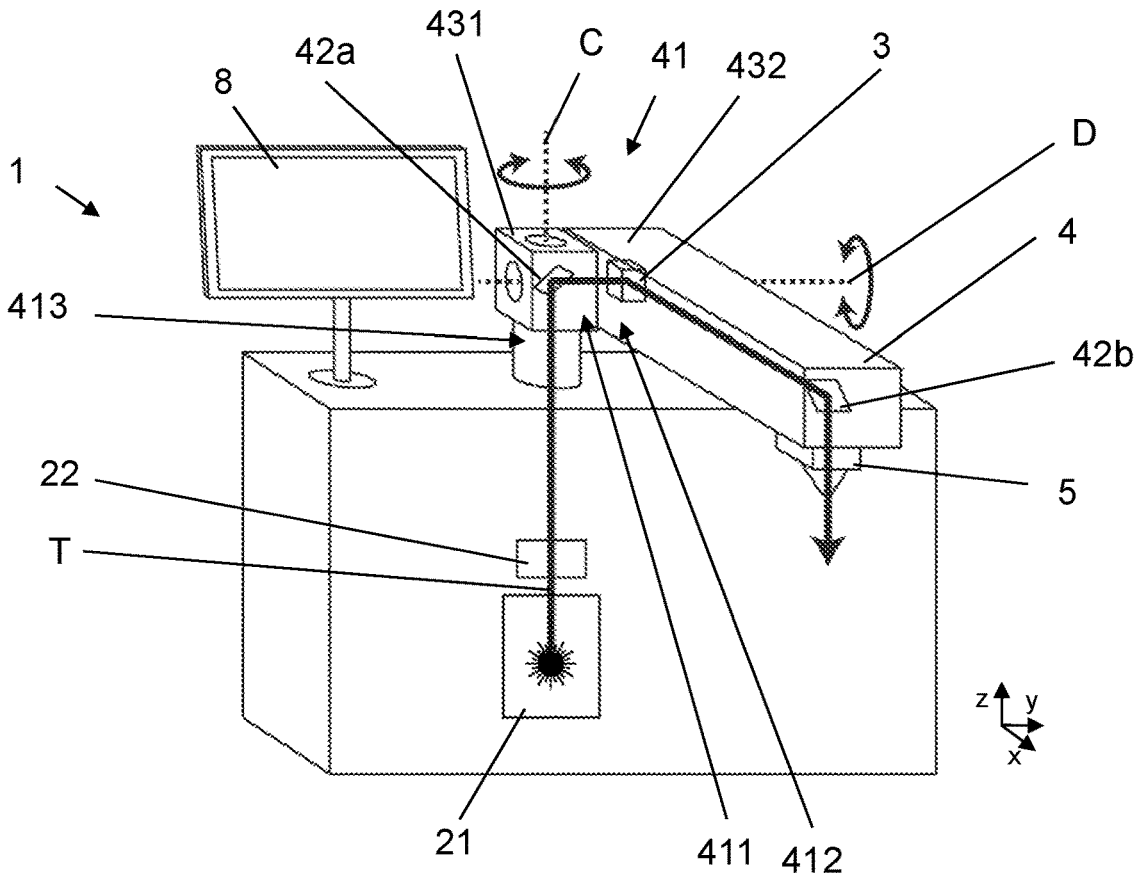
FIG. 6 shows a perspective view illustrating schematically a beam path of the treatment laser beam through a ophthalmological laser device having a vertically and horizontally rotatable arm with two joints.

FIG. 6 shows an arrangement of the arm 4 as described above with reference to FIG. 5. Additionally, the treatment laser beam T is shown as it travels from the treatment laser source 21 through the arm 4 and out of the application head 5.

The treatment laser beam T enters into the arm 4 upwards vertically (i.e. in the positive z direction) and passes into the joint 41.

Figure 7:
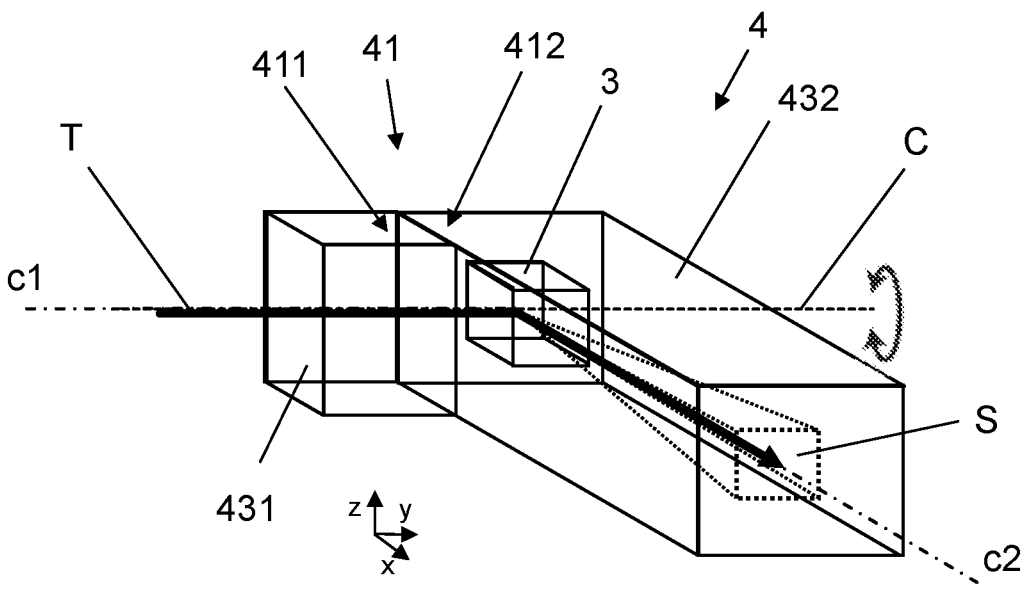
FIG. 7 shows a perspective view illustrating schematically a scanner arranged in a joint of the arm, in which the treatment laser beam enters the joint in a vertical direction and leaves the joint in a horizontal direction, the joint configured to move the arm in a vertical direction.
Figure 8:
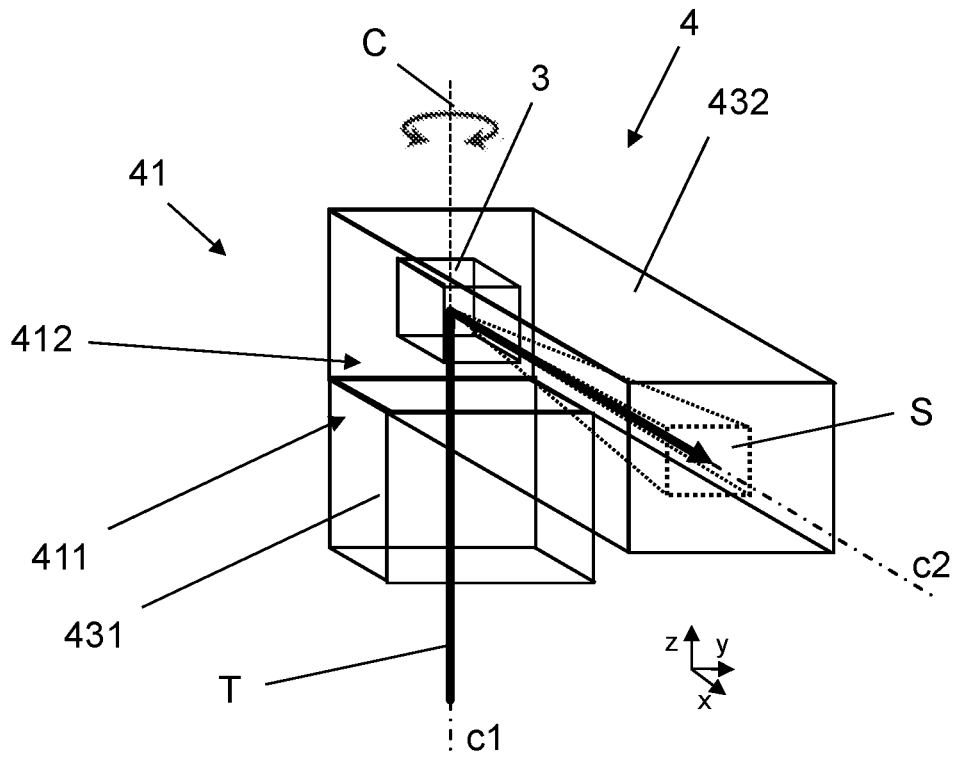
FIG. 8 shows a perspective view illustrating schematically a scanner arranged in a joint of the arm, in which the treatment laser beam enters the joint in a horizontal direction and leaves the joint in a horizontal direction, the joint configured to move the arm in a horizontal direction.

As shown in more detail in FIGS. 7 and 8, the treatment laser beam T passes through an upstream arm segment 431 into the joint 41. The treatment laser beam T, after having been deflected by the scanner 3 arranged at or in the joint 41, passes through a downstream arm segment 432 arranged downstream from the joint 41. Preferably, the treatment laser beam T is collinear with a central axis c1 of the upstream arm segment 431. The treatment laser beam T is, in a zero position, preferably also collinear with a central axis c2 of the downstream arm segment 432.

Figure 11:
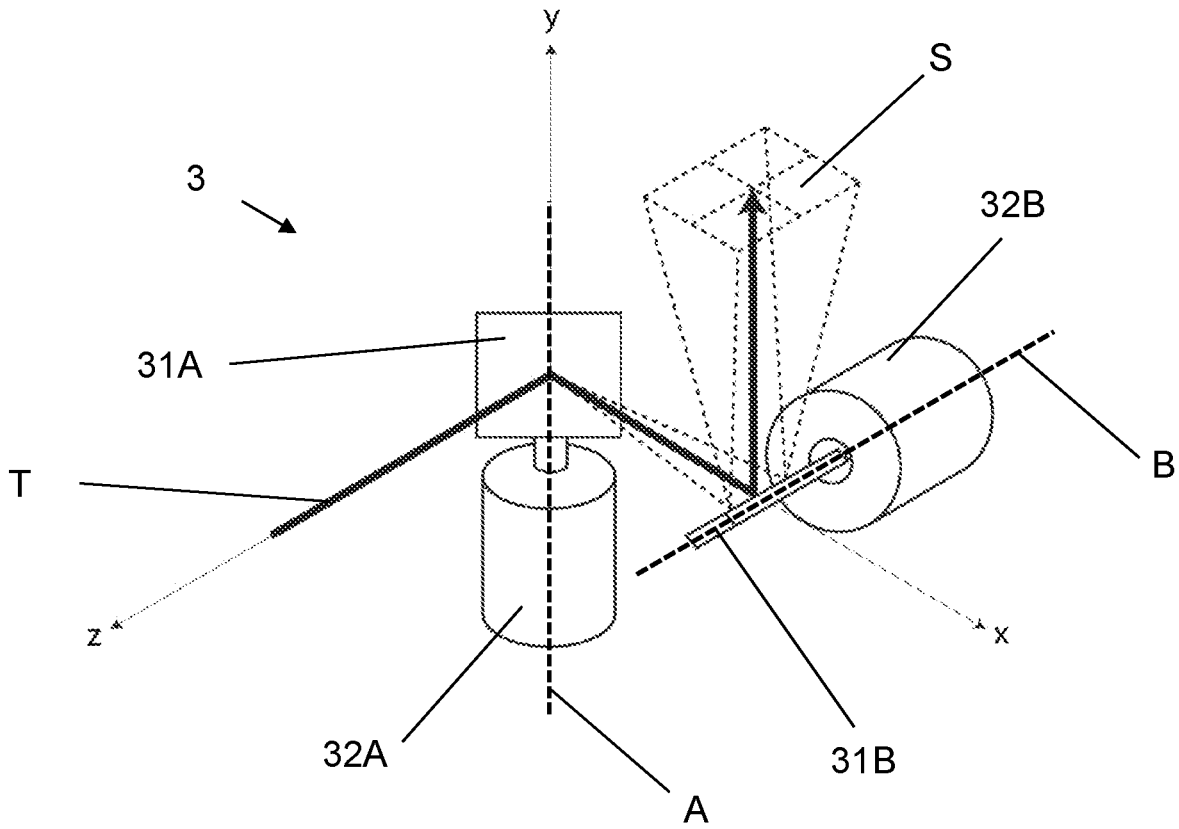
FIG. 11 shows a perspective view illustrating schematically a scanner of an ophthalmological system having two deflecting elements.

The scanner 3 deflects the treatment laser beam T within a pre-defined two-dimensional scan field S. The scan field S as illustrated, for example, in FIGS. 7, 8, 11, is exaggerated in size for ease of understanding. The two-dimensional size of the scan field S depends, of course, on the distance from the scanner 3. The scan field S may also be described by two angles (e.g., an angular deflection in the y direction and an angular deflection in the z direction) which the deflected treatment laser beam T forms with respect to a beam path of the treatment laser beam T in the zero-position. The scan field F of the scanner 3 is designed in consideration of the remaining length of the beam path in the arm 4, the application head 5, and between the application head 5 and the eye 91 of the patient 9, and, depending on the embodiment, optional transmission and/or focusing optics arranged between the scanner 3 and the eye 91 (in particular, arranged in the application head 5 and/or in an arm segment adjacent to the application head 5).

The joint 41 as shown in FIG. 6 is rotatable about two axes C, D, and has several joint parts 411, 412, 413 which move in relation to each other when the joint 41 is rotated about one or both axes C, D. An upstream stationary joint part 411 (upstream relative to the scanner 3), does not rotate about the axis D. A downstream movable joint part 412, downstream from the upstream stationary joint part 411, rotates relative to the upstream stationary joint part 411 by rotating about the axis D. A third joint part 413, further upstream from the upstream stationary joint part 411, does not rotate relative to the upstream stationary joint part 411 or the downstream stationary joint part 412 and is stationary (fixedly) arranged with respect to the base station 2.

A first mirror 42*a* arranged in the joint 41 deflects the treatment laser beam by 90° such that it travels horizontally (in particular, in the positive y direction). The first mirror 42*a* is coupled to the joint 41 such that, when the joint 41 rotates about the first axis C, which extends in the positive z direction, the first mirror 42*a* rotates with the joint 41. Thereby, regardless of the angle of the joint 41 about the first axis C, the treatment laser beam T is deflected, by the first mirror 42*a* towards the scanner 3.

The treatment laser beam T is deflected by the scanner 3 by 90°, when the scanner 3 is in a zero-position, such that the treatment laser beam T is deflected along the arm 4 towards the application head 5 in the positive x direction. In other words, the zero-position is the position of the scanner in which the treatment laser beam T travels towards the application head 5 without deviation, specifically without deviation from the default beam path which is collinear (e.g., coincident/coaxially) with a centerline of the arm 4. The zero-position is a default position of the scanner 3, i.e. a position the scanner 3 has in a default state. The zero-position can include a zero-position offset due to calibration. During treatment of an eye, the scanner 3 deflects the treatment laser beam T away from the default beam path according to the treatment model. In particular, the scanner 3 deflects the treatment laser beam T off the default beam path into the z-y plane.

A benefit of arranging the scanner 3 in the arm 4 is that one mirror is spared. The scanner 3 is arranged in the joint 41 where, in an arm 4 without a scanner 3, a mirror would be required to deflect the treatment laser beam T downstream towards the application head 5. Arranging the scanner 3 in the arm 4 has the additional benefit of placing less demands on the angular resolution of the scanner 3 than if the scanner 3 were arranged in the base station 2, as it is the case in the prior art. Nor does arranging the scanner in the arm 4 have the disadvantages of arranging the scanner directly in the application head 5, as this can lead to a bulky and unwieldy application head 5.

In an embodiment, the scanner 3 can alternatively be arranged in the upstream arm segment 431, with the first mirror 42*a* arranged in the downstream movable joint part 412.

The scanner 3 is coupled to the joint 41 such that the scanner 3, as a unit, rotates about the axis D along with the downstream section of the arm 4. Thereby the treatment laser beam T is deflected, by the scanner 3, towards the application head 5, regardless of the position of the joint 41 about the axis D (or C, for that matter).

In an embodiment, in particular in which the scanner 3 as described below with reference to FIG. 11 is used, the first mirror 42*a* is not required. In particular, the first mirror 42*a* is replaced by the first deflecting element 31A of the scanner 3.

The arm 4 includes a second mirror 42*b* configured to deflect the treatment laser beam T towards the application head 5, in particular to deflect the treatment laser beam T by 90° such that the treatment laser beam T travels in the negative z direction. In an embodiment, the second mirror 42*b* can be integrated into the application head 5.

The treatment laser beam T then passes through the application head 5 into/onto the eye 91 of the patient 9.

Figure 9:
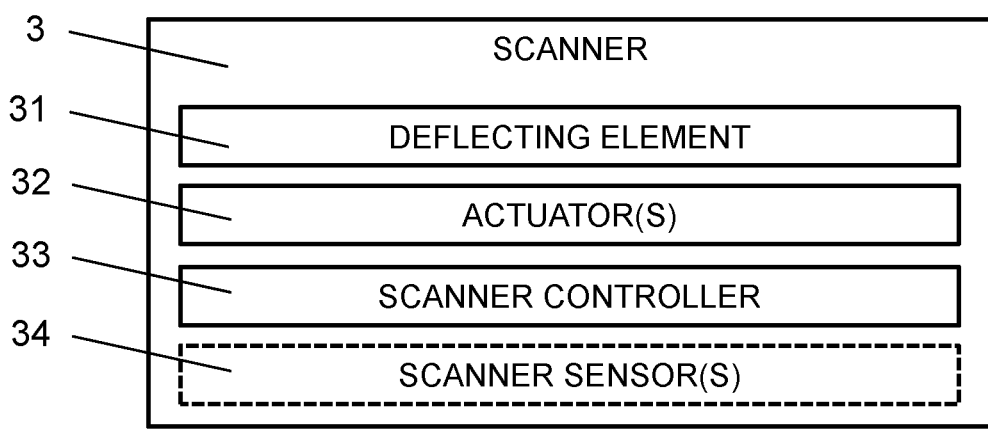
FIG. 9 shows a block diagram illustrating schematically a scanner of an ophthalmological laser device.

In the embodiment shown in FIG. 9, the scanner 3 comprises a deflecting element 31, one or more actuators 32, one or more scanner sensors 34, and a scanner controller 33. The scanner 3 has a scanner body to which the parts of the scanner 3 (i.e. the deflecting element 31, the one or more actuators 32, the one or more scanner sensors 34, and the scanner controller 33) are coupled, i.e. directly or indirectly connected. The connection includes a mechanical/structural part, but may also, additionally or alternatively, include an electrical connection for power and/or data transmission, depending on the nature of the part.

The deflecting element 31 is an element of the scanner 3 configured to deflect the treatment laser beam T. For example, the deflecting element 31 is a substantially flat surface which reflects the treatment laser beam T (more specifically, reflects a large proportion of the treatment laser beam T). The deflecting element 31 is, for example, implemented using a mirror, preferably a mirror having a low weight and/or rotational inertia, for example a beryllium mirror.

The deflecting element 31 is pivotable about a first axis A and a second axis B. The two axes A, B are arranged substantially orthogonal to each other, such that the incident treatment laser beam T is deflectable in two lateral dimensions (see FIG. 10 for additional details). The deflecting element 31 is designed such that the two axes A, B are either coincident with a (deflecting) plane of the deflecting element 31. Alternatively, the two axes A, B lie in front of or behind the deflecting plane. In any case, both axes A, B lie in a virtual plane which is substantially parallel to the deflecting plane.

Depending on the embodiment, the pivoting of the deflecting element 31 is enabled by one or more actuators 32 directly. Alternatively or additionally, the deflecting element 31 pivots about one or more pivoting elements, including, for example, an axle and bearing, a ball and socket joint, a flexure bearing or other compliant mechanism or coupling. The pivots are passive elements which move in response to externally applied forces, in particular forces applied by the actuators 32. The pivots constrain the motion of the deflecting element 31.

In an embodiment, the deflecting element 31 has, for each of the two axes A, B, one or more pivots/center of rotation which pivotably couple the deflecting element 31 to a body of the scanner 3. Preferably, the pivots for the axes A, B, are nested (i.e. the pivots which enable the deflecting element 31 to pivot about the first axis A are coupled to the deflecting element 31 and to a support element, while the pivots which enable the deflecting element 31 to pivot about the second axis B are coupled to the support element and to the body of the scanner 3).

The one or more actuators 32 are coupled to the deflecting element 31, i.e. directly or indirectly connected to the deflecting element 31. The actuators 32 are configured to cause the deflecting element 31 to pivot about the axes A, B. For example, one of the actuators 32 is configured to pivot the deflecting element 31 about the first axis A, while another of the actuators 32 is configured to pivot the deflecting element 31 about the second axis B.

Depending on the type of actuator(s) 32 used, the pivoting can be effected by rotation of the actuator(s) 32 and/or extension (and/or contraction) of the actuator(s) 32, in particular linear extension.

In an embodiment, the scanner 3, in particular the actuator 32, comprises a two-axis scan drive configured to pivot the deflecting element 31 about the axes A, B.

In an embodiment, the actuators 32 are piezo-electric actuators coupled to the deflecting element 31 and configured to pivot the deflecting element 31 by linear extension. The actuators 32 may comprise two, three, or four piezo-electric actuators. Alternatively or additionally, the actuators 32 may comprise two, three, or four electromagnetic actuators. Alternatively or additionally, the actuators 32 may comprise two, three, or four electrostatic actuators.

In an embodiment, the actuators 32 comprise one or more bimorph actuators. The bimorph actuators can also enable pivoting of the deflecting element 31, such that separate pivot(s) are not required.

The scanner 3 is configured to allow for fast and minute changes in the orientation of the deflecting element 31 about the axes A, B. In particular, the scanner is configured to have an angular resolution sufficiently high such that a minimum linear distance between treatment points in the eye 91 of the patient 9 is less than 20 micrometers. The minimum linear distance refers to a distance between spot centers of the treatment laser beam T. The treatment points in this case are arranged orthogonal to a projection axis of the beam path of the treatment beam T. The high angular resolution is achieved by using actuators 32 with a small maximum relative displacement (e.g., piezo-electric actuators allow for a relative linear displacement on the order of 0.1%), arranging the actuators 32 at a sufficient distance from their pivot axis A, B, respectively, and controlling the actuators 32 with a control signal of sufficient resolution such that small incremental changes are possible. Fast changes in the orientation of the deflecting element 31 are enabled by designing the deflecting element 31 to have a low rotational inertia. For example, the deflecting element comprises a beryllium surface to achieve a low weight.

The scanner 3 comprises one or more scanner sensors 34. The sensor(s) 34 are configured to measure a state of the scanner 3, allowing for monitoring of the scanner 3.

The scanner sensors 34 are coupled to the deflecting element 31, the actuators 32, and/or the pivots of the scanner 3 and configured to measure or detect a position of the scanner 3, for example by directly measuring a position or movement of the deflecting element 31 or a position of the pivots, or by indirectly measuring a position or movement of the actuators 32.

In an embodiment, the scanner sensors 34 are implemented as strain gauges coupled to the actuators 32. Each actuator 32 is coupled to one or more strain gauges. The strain gauges are electrically connected to the scanner 3, in particular the scanner controller 33 described below in more detail, and provide, upon having a measurement signal passed through them, strain gauge signals which are indicative of a linear extension and/or contraction of the strain gauge and therefore also of the actuator 32 to which they are coupled.

The scanner 3 comprises a scanner controller 33. The scanner controller 33 is implemented, for example, as an integrated circuit including a microprocessor. The scanner controller 33 is connected to the actuator(s) 32 and the sensor(s) 34. The scanner 3 includes, or is connected to, power electronics for powering the scanner 3. The scanner controller 33 is configured to control the scanner 3, in particular to cause a movement of the deflecting element 31 by transmitting control signals to the actuators 32. The scanner controller 33 is configured to receive sensor signals from the scanner sensors 34 (e.g., strain gauge signals from the strain gauges).

The scanner controller 33 is configured to control the scanner 3 according to a scan signal received from the control module 3. For example, the scan signal is indicative of a particular position or movement of the scanner 3 (in particular, the deflecting element 31), and the scanner controller 33 positions or moves the scanner 3 accordingly (in particular, by controlling the actuators 32). The scanner control 33 is, in an embodiment, configured to implement closed loop control.

Figure 10:
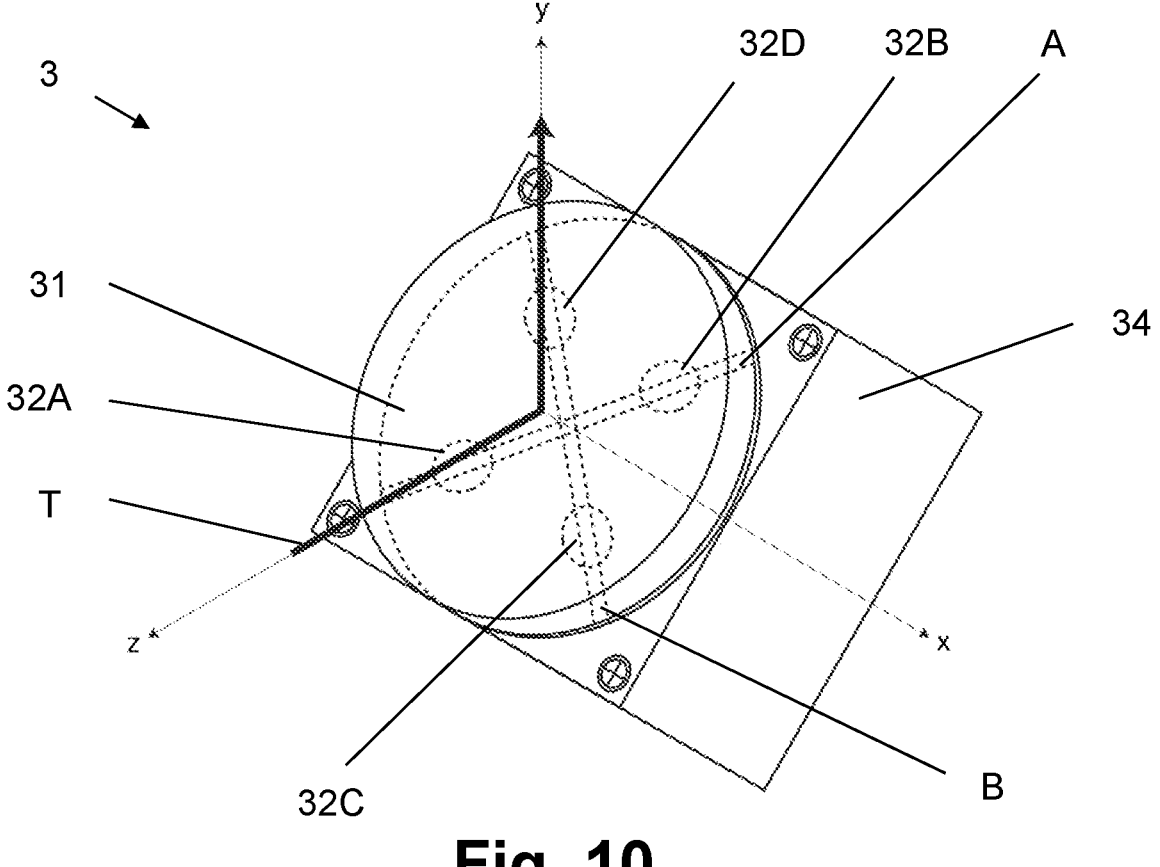
FIG. 10 shows a perspective view illustrating schematically a scanner of an ophthalmological laser device having a single deflecting element.

FIG. 10 shows a scanner 3 with a deflecting element 31. The deflecting element 31 has a circular shape with a flat surface and is designed to reflect the treatment laser beam T. As shown in the Figure, the treatment laser beam T arrives from the negative z-direction and strikes the surface of the deflecting element 31 in its center (i.e. the origin of the coordinate system used in the Figure). For purposes of illustration, the treatment laser beam T as shown in the Figure merely depicts a beam center of the treatment laser beam T—in reality the treatment laser beam T is wider than depicted. The treatment laser beam T is deflected by 90° by the deflecting element 31 and continues traveling in the positive y-direction. In the state as shown in the Figure, the deflecting element 31 is in a zero position. The zero position is a default position. The zero position is achieved, for example, with the actuators 32 in their default (i.e. unactuated) position. The zero position can also be subject to calibration. In the zero position, the treatment laser beam T is typically deflected by 90°.

By pivoting the deflecting element 31 about one or both of the axes A, B, the treatment laser beam T is deflected from the y-direction such that the vector of the deflected treatment laser beam T has a vector component in the x-direction and/or the z-direction in the coordinates of the Figure. However, this translates to, for example, a deflection into the x and y direction in the (quasi) two-dimensional treatment plane of the surface of the eye 91.

In the embodiment shown, the axes A, B about which the deflecting element 31 pivots are arranged at 45° to the x-direction in the plane of the surface of the deflecting element 31. Further, the plane formed by the incident and deflected treatment laser beam T is orthogonal to the x-direction (i.e. both the incident treatment laser beam T and the deflected treatment laser beam T are orthogonal to the x-direction), and therefore the axes A, B both form an angle of 45° to the plane formed by the incident and deflected treatment laser beam T. FIG. 10 further shows schematically four actuators 32A, 32B, 32C 32D, which are configured to pivot the deflecting element 31.

FIG. 11 shows a scanner 3 including two deflecting elements 31A, 31B which are driven by actuators 32A, 32B, respectively. The actuators 32A, 32B, are, for example, galvanometers.

In the default zero position, the first deflecting element 31A deflects the incident treatment laser beam by 90°, such that it is deflected from the negative z direction towards the positive x direction. The first deflecting element 31A rotates about an axis parallel to they direction, such that it can scan (i.e., dynamically deflect) the treatment laser beam T along a line parallel to the z direction.

In a default zero position, the second deflecting element 31B deflects the incident treatment laser beam by 90°, such that it is deflected from the positive x direction towards the positive y direction.

The second deflecting element 31A rotates about an axis parallel to the z direction, such that it can scan (i.e., dynamically deflect) the treatment laser beam T along a line parallel to the x direction.

In sum, therefore, the two deflecting elements 31A, 31B deflect the treatment laser beam T by 90°, from the negative z direction into the positive y direction, when both deflecting elements 31A, 31B are in the zero position.

The result of both deflecting elements 31A, 31B, scanning the treatment laser beam T is that the treatment laser beam T is deflected in two dimensions in a plane parallel to the x-z plane.

The above-described embodiments of the disclosure are exemplary and the person skilled in the art knows that at least some of the components and/or steps described in the embodiments above may be rearranged, omitted, or introduced into other embodiments without deviating from the scope of the present disclosure.

The invention claimed is:

1. An ophthalmological laser device for treatment of eye tissue comprising:

a base station having a treatment laser source configured to generate a treatment laser beam;

an application head;

an arm arranged between the base station and the application head, wherein the arm is configured to provide a beam path for the treatment laser beam, the arm having a joint; and a scanner arranged in the joint and configured to dynamically deflect the treatment laser beam about two axes, wherein the beam path for the treatment laser beam upstream of the scanner is collinear with an axis of rotation of the joint and an orientation of the scanner is dependent on a movement of the joint.

2. The ophthalmological laser device of claim 1, wherein the scanner comprises a deflecting element pivotable about the two axes.

3. The ophthalmological laser device of claim 1, wherein the scanner comprises a first deflecting element pivotable about a first axis of the two axes and a second deflecting element pivotable about a second axis of the two axes.

4. The ophthalmological laser device of claim 1, wherein the joint comprises an upstream stationary joint part and a downstream movable joint part, and the scanner is arranged at the joint by being coupled to the downstream movable joint part such that the scanner moves together with the downstream movable joint part.

5. The ophthalmological laser device of claim 4, wherein the scanner is coupled to the joint by a mechanical coupling.

6. The ophthalmological laser device of claim 1, wherein the treatment laser beam incident on the scanner is a collimated treatment laser beam.

7. The ophthalmological laser device of claim 1, wherein the treatment laser beam deflected by the scanner is a collimated treatment laser beam.

8. The ophthalmological laser device of claim 1, wherein the arm includes an upstream arm segment which is upstream from the joint and a downstream arm segment which is downstream from the joint; and the treatment laser beam in the upstream arm segment is collinear with a centerline of the upstream arm segment, and the scanner is arranged such that the treatment laser beam in the downstream arm segment is collinear with a centerline of the downstream arm segment, regardless of a movement of the joint, when the scanner is in a zero-position, the zero-position being a default position in that the scanner does not steer the treatment laser beam off a center axis of the beam path.

9. The ophthalmological laser device of claim 8, further comprising a mirror arranged in the upstream stationary joint part, the mirror being configured to deflect the treatment laser beam onto the scanner.

10. The ophthalmological laser device of claim 9, wherein the joint has an axis of rotation which is not collinear with a centerline of the upstream arm segment and the mirror is configured to deflect the treatment laser beam in a direction collinear with the axis of rotation of the joint and coincident with the scanner.

11. The ophthalmological laser device of claim 9, wherein the joint is rotatable about a first axis and a second axis, wherein the mirror is coupled to the joint such that the mirror rotates about the first axis and the scanner is coupled to the joint such that the scanner rotates about the second axis.

12. The ophthalmological laser device of claim 1, wherein the arm comprises a plurality of joints arranged between the base station and the application head, and the scanner is arranged in a particular joint of the plurality of joints most adjacent to the application head.

13. The ophthalmological laser device of claim 1, wherein the scanner comprises an electromagnetic scanner.

14. The ophthalmological laser device of claim 1, wherein the scanner comprises a piezoelectric scanner.

15. The ophthalmological laser device of claim 1, wherein the scanner comprises an electrostatic scanner.

* * * * *